(12) United States Patent
Jimenez et al.

(10) Patent No.: US 12,102,781 B2
(45) Date of Patent: Oct. 1, 2024

(54) REINFORCEMENT FOR IRRIGATED ELECTROPHYSIOLOGY BALLOON CATHETER WITH FLEXIBLE-CIRCUIT ELECTRODES

(71) Applicant: BIOSENSE WEBSTER (ISRAEL) LTD., Yokneam (IL)

(72) Inventors: Jose Jimenez, Ontario, CA (US);
Michael Banando, Glendora, CA (US);
Cuong Pham, Westminster, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 382 days.

(21) Appl. No.: 16/432,392

(22) Filed: Jun. 5, 2019

(65) Prior Publication Data

US 2020/0001054 A1  Jan. 2, 2020

Related U.S. Application Data

(60) Provisional application No. 62/692,439, filed on Jun. 29, 2018.

(51) Int. Cl.
*A61B 18/14* (2006.01)
*A61B 5/00* (2006.01)
(Continued)

(52) U.S. Cl.
CPC ....... *A61M 25/1002* (2013.01); *A61B 5/6853* (2013.01); *A61B 18/1492* (2013.01);
(Continued)

(58) Field of Classification Search
CPC ........ A61B 1/00082; A61B 2018/0016; A61B 2018/00214; A61B 2018/0022;
(Continued)

(56) References Cited

U.S. PATENT DOCUMENTS

| D123,782 S | 12/1940 | Lux |
|---|---|---|
| 3,316,896 A | 5/1967 | Thomasset |

(Continued)

FOREIGN PATENT DOCUMENTS

| CN | 101422637 A | 5/2009 |
|---|---|---|
| CN | 102271607 A | 12/2011 |

(Continued)

OTHER PUBLICATIONS

YouTube, "Intensity™ CX4 Professional E-Stim/Ultrasound Combo", Dec. 22, 2015, Retrieved from internet [https://www.youtube.com/watch?v=76s1QkMWJME], retrieved on Nov. 19, 2020, 1 page.

(Continued)

*Primary Examiner* — Jaymi E Della
(74) *Attorney, Agent, or Firm* — Claderon Safran & Wright, P.C.; Etan S. Chatlynne (57) ABSTRACT

A balloon of a balloon catheter must be able to withstand fatigue to its componentry caused by multiple cycles of repeat motions, such as deployment from a lumen of the catheter, expanding the balloon, collapsing the balloon, and withdrawal of the balloon into the lumen. The catheter balloon may include plurality of electrode substrates, each including a plurality of tails. A reinforcement component, which may be a portion of another balloon, may be disposed over at least some of the plurality of tails and attached to the membrane. Where tails are provided on the proximal and distal ends of the balloon, two reinforcement mechanisms may be used.

19 Claims, 7 Drawing Sheets

(51) Int. Cl.
*A61M 25/10* (2013.01)
*A61B 18/00* (2006.01)

(52) U.S. Cl.
CPC ............ *A61B 2018/00011* (2013.01); *A61B 2018/0022* (2013.01); *A61B 2018/00238* (2013.01); *A61B 2218/002* (2013.01); *A61B 2562/164* (2013.01); *A61M 2025/1043* (2013.01); *A61M 2025/1081* (2013.01); *A61M 2025/1093* (2013.01)

(58) Field of Classification Search
CPC ........... A61B 2018/00238; A61B 2018/00285; A61B 2018/00577; A61B 2218/002; A61B 2562/164; A61B 5/6853; A61M 25/10–2025/1097
See application file for complete search history.

(56) References Cited

U.S. PATENT DOCUMENTS

| | | |
|---|---|---|
| 4,232,676 A | 11/1980 | Herczog |
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,391,199 A | 2/1995 | Ben-Haim |
| 5,429,617 A | 7/1995 | Hammersmark et al. |
| 5,582,609 A | 12/1996 | Swanson et al. |
| 5,584,830 A | 12/1996 | Ladd et al. |
| 5,702,386 A | 12/1997 | Stern et al. |
| 5,797,903 A | 8/1998 | Swanson et al. |
| 5,860,974 A | 1/1999 | Abele |
| 5,971,983 A | 10/1999 | Lesh |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,142,993 A | 11/2000 | Whayne et al. |
| 6,164,283 A | 12/2000 | Lesh |
| 6,171,275 B1 | 1/2001 | Webster, Jr. |
| 6,176,832 B1 | 1/2001 | Habu et al. |
| 6,226,542 B1 | 5/2001 | Reisfeld |
| 6,239,724 B1 | 5/2001 | Doron et al. |
| 6,301,496 B1 | 10/2001 | Reisfeld |
| 6,325,777 B1 | 12/2001 | Zadno-Azizi et al. |
| 6,332,089 B1 | 12/2001 | Acker et al. |
| 6,380,957 B1 | 4/2002 | Banning |
| 6,402,740 B1 | 6/2002 | Ellis et al. |
| D462,389 S | 9/2002 | Provence et al. |
| 6,471,693 B1 | 10/2002 | Carroll et al. |
| 6,484,118 B1 | 11/2002 | Govari |
| 6,522,930 B1 | 2/2003 | Schaer et al. |
| 6,618,612 B1 | 9/2003 | Acker et al. |
| 6,656,174 B1 | 12/2003 | Hegde et al. |
| 6,690,963 B2 | 2/2004 | Ben-Haim et al. |
| 6,814,733 B2 | 11/2004 | Schwartz et al. |
| 6,892,091 B1 | 5/2005 | Ben-Haim et al. |
| 6,893,433 B2 | 5/2005 | Lentz |
| 6,986,744 B1 | 1/2006 | Krivitski |
| 6,997,924 B2 | 2/2006 | Schwartz et al. |
| 7,156,816 B2 | 1/2007 | Schwartz et al. |
| 7,340,307 B2 | 3/2008 | Maguire et al. |
| 7,442,190 B2 | 10/2008 | Abboud et al. |
| 7,536,218 B2 | 5/2009 | Govari et al. |
| 7,756,576 B2 | 7/2010 | Levin |
| 7,842,031 B2 | 11/2010 | Abboud et al. |
| 8,048,032 B2 | 11/2011 | Root et al. |
| 8,231,617 B2 | 7/2012 | Satake |
| 8,267,932 B2 | 9/2012 | Baxter et al. |
| 8,357,152 B2 | 1/2013 | Govari et al. |
| D682,289 S | 5/2013 | Dijulio et al. |
| D682,291 S | 5/2013 | Baek et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,974,450 B2 | 3/2015 | Brannan |
| 8,998,893 B2 | 4/2015 | Avitall |
| D729,263 S | 5/2015 | Ahn et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| D783,037 S | 4/2017 | Hariharan et al. |
| 9,655,677 B2 | 5/2017 | Salahieh et al. |
| D791,805 S | 7/2017 | Segars |
| 9,795,442 B2 | 10/2017 | Salahieh et al. |
| D861,717 S | 10/2019 | Brekke et al. |
| 10,688,278 B2 | 6/2020 | Beeckler et al. |
| 2001/0031961 A1 | 10/2001 | Hooven |
| 2002/0002369 A1 | 1/2002 | Hood |
| 2002/0065455 A1 | 5/2002 | Ben-Haim et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0050637 A1 | 3/2003 | Maguire et al. |
| 2003/0060820 A1 | 3/2003 | Maguire et al. |
| 2003/0120150 A1 | 6/2003 | Govari |
| 2004/0068178 A1 | 4/2004 | Govari |
| 2004/0122445 A1 | 6/2004 | Butler et al. |
| 2004/0225285 A1 | 11/2004 | Gibson |
| 2005/0059862 A1 | 3/2005 | Phan |
| 2005/0070887 A1 | 3/2005 | Taimisto et al. |
| 2005/0119686 A1 | 6/2005 | Clubb |
| 2006/0013595 A1 | 1/2006 | Trezza et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0276212 A1 | 11/2007 | Fuimaono et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1* | 2/2008 | Phan ................ A61M 25/1006 604/108 |
| 2008/0140072 A1 | 6/2008 | Stangenes et al. |
| 2008/0183132 A1* | 7/2008 | Davies ................ A61M 25/104 604/103.09 |
| 2008/0188912 A1 | 8/2008 | Stone et al. |
| 2008/0202637 A1 | 8/2008 | Hector et al. |
| 2008/0249463 A1 | 10/2008 | Pappone et al. |
| 2008/0262489 A1 | 10/2008 | Steinke |
| 2009/0163890 A1 | 6/2009 | Clifford et al. |
| 2009/0171274 A1 | 7/2009 | Harlev et al. |
| 2009/0182318 A1 | 7/2009 | Abboud et al. |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0160906 A1 | 6/2010 | Jarrard |
| 2010/0204560 A1 | 8/2010 | Salahieh et al. |

(56) References Cited

U.S. PATENT DOCUMENTS

| | | |
|---|---|---|
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1* | 3/2012 | Salahieh ............ A61B 1/00181 606/33 |
| 2012/0079427 A1 | 3/2012 | Carmichael et al. |
| 2012/0101413 A1 | 4/2012 | Beetel et al. |
| 2012/0143177 A1 | 6/2012 | Avitall |
| 2012/0191079 A1 | 7/2012 | Moll et al. |
| 2013/0085360 A1 | 4/2013 | Grunewald |
| 2013/0090649 A1* | 4/2013 | Smith ............... A61B 18/1492 606/41 |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165925 A1 | 6/2013 | Mathur et al. |
| 2013/0165941 A1 | 6/2013 | Murphy |
| 2013/0165990 A1 | 6/2013 | Mathur et al. |
| 2013/0261692 A1 | 10/2013 | Cardinal et al. |
| 2013/0274562 A1* | 10/2013 | Ghaffari ............ A61B 5/6833 601/3 |
| 2013/0274658 A1* | 10/2013 | Steinke ............. A61B 18/1492 606/41 |
| 2013/0282084 A1 | 10/2013 | Mathur et al. |
| 2013/0318439 A1 | 11/2013 | Landis et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | Deboer et al. |
| 2014/0243821 A1 | 8/2014 | Salahieh et al. |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2014/0378803 A1 | 12/2014 | Geistert et al. |
| 2015/0005799 A1 | 1/2015 | Lindquist et al. |
| 2015/0018818 A1 | 1/2015 | Willard et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1* | 4/2015 | Byrne ............... A61M 25/1029 604/103.02 |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0183877 A1 | 6/2016 | Williams et al. |
| 2016/0196635 A1 | 7/2016 | Cho et al. |
| 2016/0256305 A1 | 9/2016 | Longo et al. |
| 2016/0374748 A9* | 12/2016 | Salahieh ............ A61B 18/1492 606/34 |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2017/0348049 A1* | 12/2017 | Vrba ................. A61B 18/1492 |
| 2018/0074693 A1 | 3/2018 | Jones et al. |
| 2018/0092688 A1 | 4/2018 | Tegg |
| 2018/0110562 A1 | 4/2018 | Govari et al. |
| 2018/0161093 A1 | 6/2018 | Basu et al. |
| 2018/0256247 A1 | 9/2018 | Govari et al. |
| 2018/0333162 A1 | 11/2018 | Saab |
| 2018/0368927 A1 | 12/2018 | Lyons et al. |
| 2019/0297441 A1 | 9/2019 | Dehe et al. |
| 2019/0298441 A1 | 10/2019 | Clark et al. |
| 2020/0008869 A1 | 1/2020 | Byrd |
| 2020/0015693 A1 | 1/2020 | Beeckler et al. |
| 2020/0085497 A1 | 3/2020 | Zhang et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| EP | 0779059 A1 | 6/1997 |
| EP | 1790304 A2 | 5/2007 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |
| EP | 3653153 A1 | 5/2020 |
| JP | H06261951 A | 9/1994 |
| JP | H1176233 A | 3/1999 |
| JP | 2000504242 A | 4/2000 |
| JP | 2004504314 A | 2/2004 |
| JP | 2005052424 A | 3/2005 |
| JP | 2008538986 A | 11/2008 |
| JP | 2009261609 A | 11/2009 |
| JP | 2010507404 A | 3/2010 |
| JP | 2010088697 A | 4/2010 |
| JP | 2012024156 A | 2/2012 |
| JP | 2012508083 A | 4/2012 |
| JP | 2013013726 A | 1/2013 |
| JP | 2013078587 A | 5/2013 |
| JP | 2013529109 A | 7/2013 |
| JP | 2014509218 A | 4/2014 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016093502 A | 5/2016 |
| JP | 2016515442 A | 5/2016 |
| JP | 2016116863 A | 6/2016 |
| JP | 2016534842 A | 11/2016 |
| JP | 2017202305 A | 11/2017 |
| JP | 2017202306 A | 11/2017 |
| JP | 2018075365 A | 5/2018 |
| WO | 9605768 A1 | 2/1996 |
| WO | 0056237 A2 | 9/2000 |
| WO | 02102231 A2 | 12/2002 |

(56) References Cited

FOREIGN PATENT DOCUMENTS

| | | | |
|---|---|---|---|
| WO | 2005041748 A2 | 5/2005 | |
| WO | 2006055654 A1 | 5/2006 | |
| WO | 2008049087 A2 | 4/2008 | |
| WO | 2011143468 A2 | 11/2011 | |
| WO | 2013049601 A2 | 4/2013 | |
| WO | 2013052919 A2 | 4/2013 | |
| WO | 2013154776 A2 | 10/2013 | |
| WO | 2014123983 A2 | 8/2014 | |
| WO | 2014168987 A1 | 10/2014 | |
| WO | 2015049784 A1 | 4/2015 | |
| WO | 2015200518 A1 | 12/2015 | |
| WO | 2016084215 A1 | 6/2016 | |
| WO | 2016183337 A2 | 11/2016 | |
| WO | 2016210437 A1 | 12/2016 | |
| WO | 2017024306 A1 | 2/2017 | |
| WO | WO-2017087549 A1 * | 5/2017 | ......... A61B 1/00009 |
| WO | 2017163400 A1 | 9/2017 | |
| WO | 2018106569 A1 | 6/2018 | |
| WO | 2019095020 A1 | 5/2019 | |

OTHER PUBLICATIONS

YouTube, "New Interface TactiCath Contact Force Ablation Catheter", Nov. 26, 2013, retrieved from internet [https://www.youtube.com/watch?v=aYvYO8Hpylg], retrieved on Nov. 19, 2020, 1 page.
European Search Report for European Application No. 19183327, dated Nov. 21, 2019, 8 pages.
Extended European Search Report for European Application No. EP20195648.9, dated Feb. 12, 2021, 8 pages.
Extended European Search Report for Application No. EP17168393.1 dated Dec. 15, 2017, 12 pages.
Extended European Search Report for Application No. EP17168513.4 dated Sep. 18, 2017, 11 pages.
Extended European Search Report for European Application No. 17201434.2, dated Feb. 1, 2018, 9 pages.
Extended European Search Report for European Application No. EP15201723.2, dated May 11, 2016, 7 pages.
Extended European Search Report for European Application No. EP17168518.3, dated Sep. 20, 2017, 9 pages.
Extended European Search Report for European Application No. EP17173893.3, dated Nov. 6, 2017, 8 pages.
Extended European Search Report for European Application No. EP17205876.0, dated Jun. 1, 2018, 13 pages.
Extended European Search Report for European Application No. EP20153872.5, dated May 7, 2020, 8 pages.
International Search Report and Written Opinion for Application No. PCT/IB2019/056381, dated Dec. 17, 2019, 10 pages.
International Search Report and Written Opinion for Application No. PCT/IB2019/052313, dated Jul. 22, 2019, 08 pages.
Partial European Search Report for Application No. EP17168393.1 dated Sep. 13, 2017, 13 pages.
Partial European Search Report for European Application No. EP17205876.0, dated Feb. 22, 2018, 10 pages.
Extended European Search Report for European Application No. EP19177365.4, dated Nov. 8, 2019, 7 pages.
Haines, D.E., et al., "The Promise of Pulsed Field Ablation," Dec. 2019, vol. 19 (12), pp. 10.

* cited by examiner

REINFORCEMENT FOR IRRIGATED ELECTROPHYSIOLOGY BALLOON CATHETER WITH FLEXIBLE-CIRCUIT ELECTRODES

CROSS-REFERENCE TO RELATED APPLICATION

The present application claims priority under 35 U.S.C. § 119 to U.S. Provisional Patent Application No. 62/692,439, filed Jun. 29, 2018. The entire contents of this application is incorporated by reference herein in its entirety.

FIELD

The subject matter disclosed herein relates to electrophysiologic catheters, particularly those capable of ablating cardiac tissue via electrodes disposed on a balloon surface.

BACKGROUND

Ablation of cardiac tissue has been used to treat cardiac arrhythmias. Ablative energies are typically provided to cardiac tissue by a tip portion, which can deliver ablative energy alongside the tissue to be ablated. Some of these catheters administer ablative energy from various electrodes disposed on or incorporated into three-dimensional structures, e.g., wire baskets and balloons.

SUMMARY OF THE DISCLOSURE

A balloon of a balloon catheter must be able to withstand fatigue to its componentry caused by multiple cycles of repeat motions, such as deployment from a lumen of the catheter, expanding the balloon, collapsing the balloon, and withdrawal of the balloon back into the lumen. Such a catheter balloon may comprise a membrane including a proximal end and a distal end. A plurality of substrates, each including a plurality of tails, may be disposed about the membrane. A reinforcement may be disposed over at least some of the plurality of tails and attached to the membrane. The reinforcement may comprise a portion of an unassembled catheter balloon. Alternatively, or additionally, the reinforcement may have a horn-like shape. In any of the embodiments, the membrane may comprise polyethylene terephthalate, polyurethane, PELLETHANE®, or PEBAX®.

Further, in any of the embodiments, the plurality of tails may include a plurality of proximal tails and a plurality of distal tails. The plurality of proximal tails may be disposed proximate to the proximal end of the balloon and the plurality of distal tails may be disposed proximate to the distal end of the balloon. The reinforcement may be disposed over the plurality of proximal tails or over the plurality of distal tails. A first and second reinforcement may be provided such that the first reinforcement may be disposed over the plurality of distal tails and the second reinforcement may be disposed over the plurality of proximal tails. Where two reinforcements are employed, they may be symmetric with each other.

In any of the foregoing embodiments, the membrane may further include irrigation apertures disposed therethrough. Additionally, the membrane may further include a plurality of ablation electrodes. These electrodes may be disposed on the substrates. Furthermore, a filament may be disposed between the membrane and at least one of the plurality of tails. The filament may comprise a liquid-crystal polymer, such as VECTRAN™.

The balloon may be incorporated or connected to a distal end of a catheter. The catheter may include a shaft having a first shaft portion and second shaft portion at least partially disposed within the first shaft portion. A ring or rings may be disposed about at least a portion of the first reinforcement, second reinforcement (if included), or both to aid in connecting the balloon to the catheter. Additionally, the catheter shaft may have telescoping functionality such that the second shaft portion may be disposed within the first shaft portion.

The catheter may be used according to various methods and variations. For example, after receiving the catheter, the balloon may be deployed from the catheter's lumen. Then the balloon may be expanded, collapsed, and withdrawn back into the lumen. These steps of deploying, expanding, collapsing, and withdrawing may be repeated between five to twenty times. Further, the ablation electrodes may be activated. Typically, the ablation electrodes may be activated after each expanding step and before each collapsing step.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Overview

Ablation of cardiac tissue to correct a malfunctioning heart is a well-known procedure. Typically, to successfully ablate, cardiac electropotentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation.

An ablation catheter may include a lumen, and a balloon may be deployed through the catheter lumen. A multi-layer flexible metal structure is attached to an exterior wall or membrane of the balloon. The structure comprises a plurality of electrode groups arranged circumferentially about the longitudinal axis, where each electrode group comprises multiple ablation electrodes, typically arranged longitudinally.

Each electrode group may also include at least one micro-electrode that is insulated physically and electrically from the ablation electrodes in its group.

Each electrode group may also include at least a thermocouple.

In some embodiments, each electrode group has a micro-electrode and a thermocouple formed at a common location.

Using a single catheter, with the three functionalities of ability to perform ablation, electropotential measurement, and temperature measurement, simplifies cardiac ablation procedures.

System Description

Figure 1:
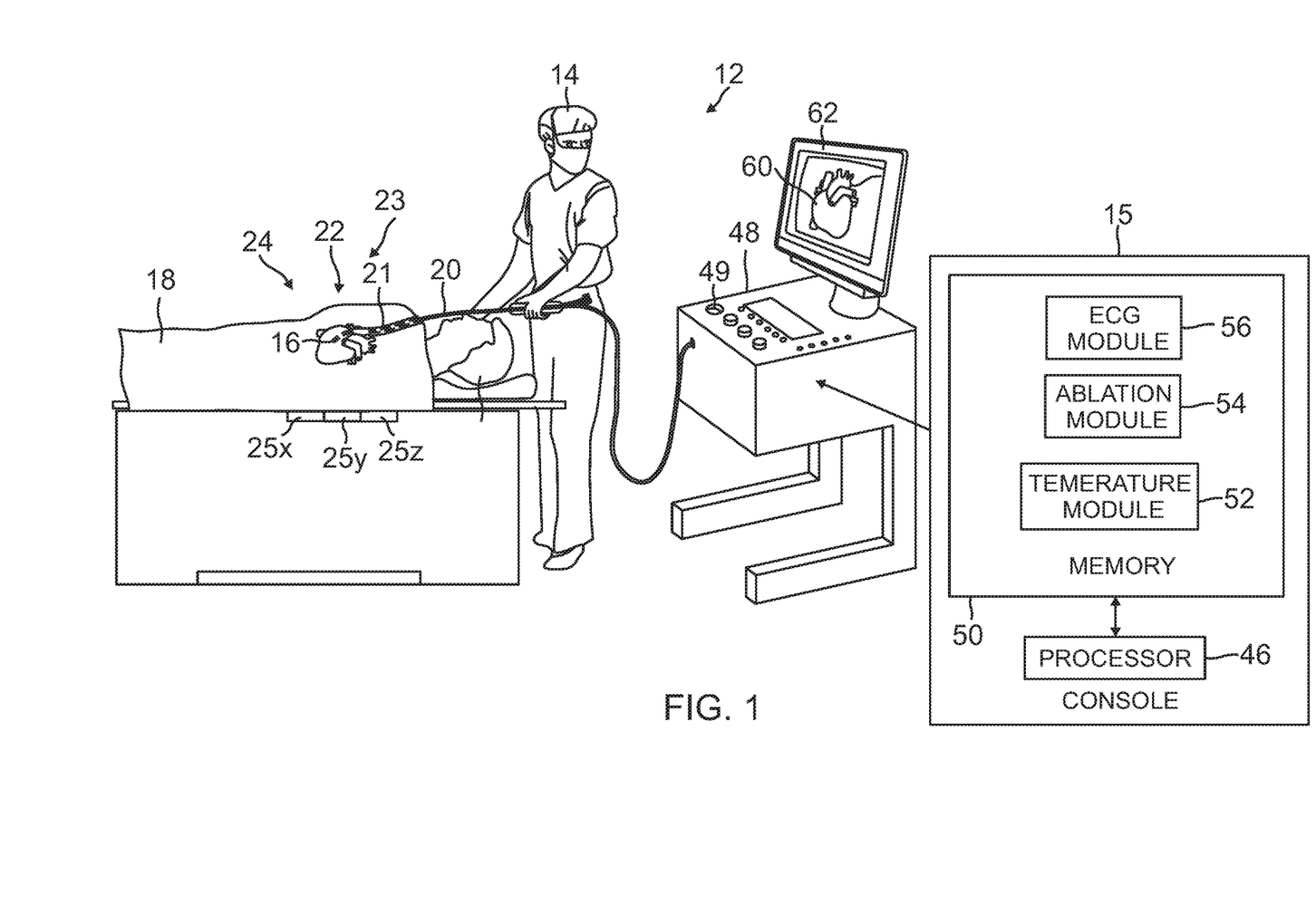
FIG. 1 is a schematic illustration of an invasive medical procedure.

FIG. 1 is a schematic illustration of an invasive medical procedure using apparatus 12, according to an embodiment. The procedure is performed by a medical professional 14, and, by way of example, the procedure in the description hereinbelow is assumed to comprise ablation of a portion of a myocardium 16 of the heart of a human patient 18. However, it is understood that embodiments disclosed herein are not merely applicable to this specific procedure and may include substantially any procedure on biological tissue or on non-biological materials.

Figure 2:
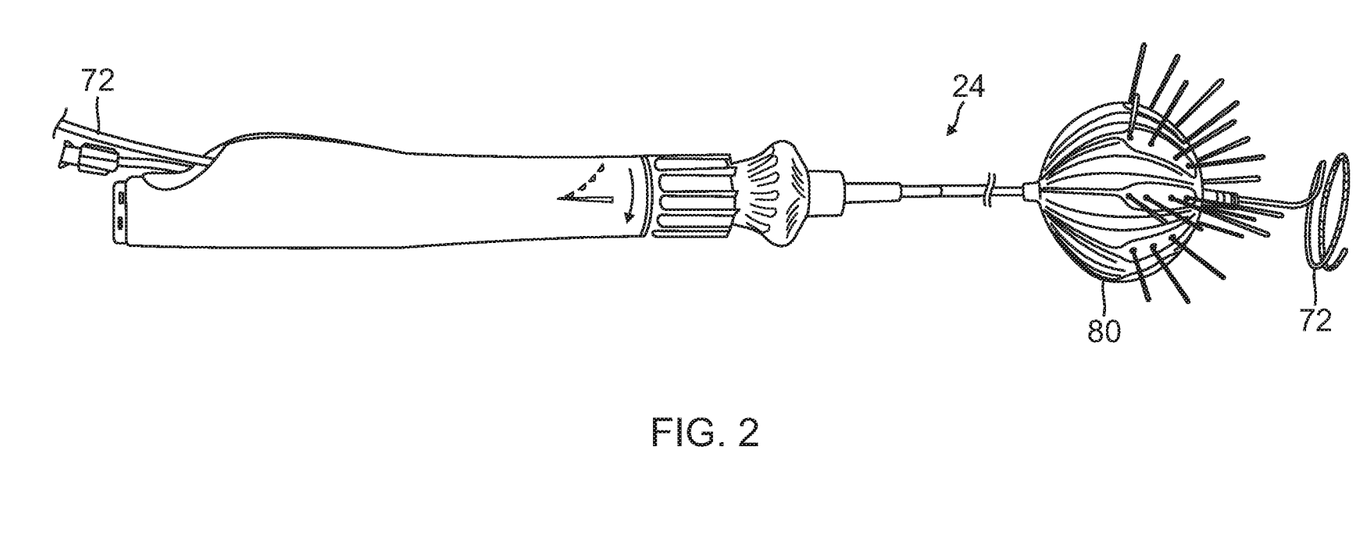
FIG. 2 is a top view of a catheter with a balloon in an expanded state, in use with a lasso catheter.

To perform the ablation, medical professional 14 inserts a probe 20 into a sheath 21 that has been pre-positioned in a lumen of the patient. Sheath 21 is positioned so that a distal end 22 of probe 20 enters the heart of the patient. A diagnostic/therapeutic catheter 24 (e.g., a balloon catheter), which is described in more detail below with reference to FIG. 2, is deployed through a lumen 23 of the probe 20 and exits from a distal end of the probe 20.

As shown in FIG. 1, apparatus 12 is controlled by a system processor 46, which is in an operating console 15 of the apparatus. Console 15 comprises controls 49 which are used by professional 14 to communicate with the processor. During the procedure, the processor 46 typically tracks a location and an orientation of the distal end 22 of the probe 20, using any method known in the art. For example, processor 46 may use a magnetic tracking method, wherein magnetic transmitters 25X, 25Y and 25Z external to the patient 18 generate signals in coils positioned in the distal end of the probe 20. The CARTO® system (available from Biosense Webster, Inc. of Irvine, Calif.) uses such a tracking method.

The software for the processor 46 may be downloaded to the processor in electronic form, over a network, for example. Alternatively, or additionally, the software may be provided on non-transitory tangible media, such as optical, magnetic, or electronic storage media. The tracking of the distal end 22 is may be displayed on a three-dimensional representation 60 of the heart of the patient 18 on a screen 62. However, it may be displayed two-dimensionally, e.g., by fluoroscopy or MRI.

To operate apparatus 12, the processor 46 communicates with a memory 50, which has many modules used by the processor to operate the apparatus. Thus, the memory 50 comprises a temperature module 52, an ablation module 54, and an electrocardiograph (ECG) module 56, the functions of which are described below. The memory 50 typically comprises other modules, such as a force module for measuring the force on the distal end 22, a tracking module for operating the tracking method used by the processor 46, and an irrigation module allowing the processor to control irrigation provided for the distal end 22. For simplicity, such other modules are not illustrated in FIG. 1. The modules may comprise hardware as well as software elements. For example, module 54 may include a radio-frequency generator with at least one output or output channel, e.g., ten outputs or ten output channels. Each of the outputs may be separately and selectively activated or deactivated by a switch. That is, each switch may be disposed between the signal generator and a respective output. Thus, a generator with ten outputs would include ten switches. These outputs may each be individually coupled to electrodes on an ablation catheter, e.g., the ten electrodes 33 on balloon 80, described in further detail below. Such an electrical connection may be achieved by establishing an electrical path between each output and each electrode. For example, each output may be connected to a corresponding electrode by one or more wires or suitable electrical connectors. Thus, in some embodiments, an electrical path may include at least one wire. In some embodiments, the electrical path may further include an electrical connector and at least a second wire. Thus, electrodes 33 may be selectively activated and deactivated with the switches to receive radiofrequency energy separately from each of the other electrodes.

Figure 3:
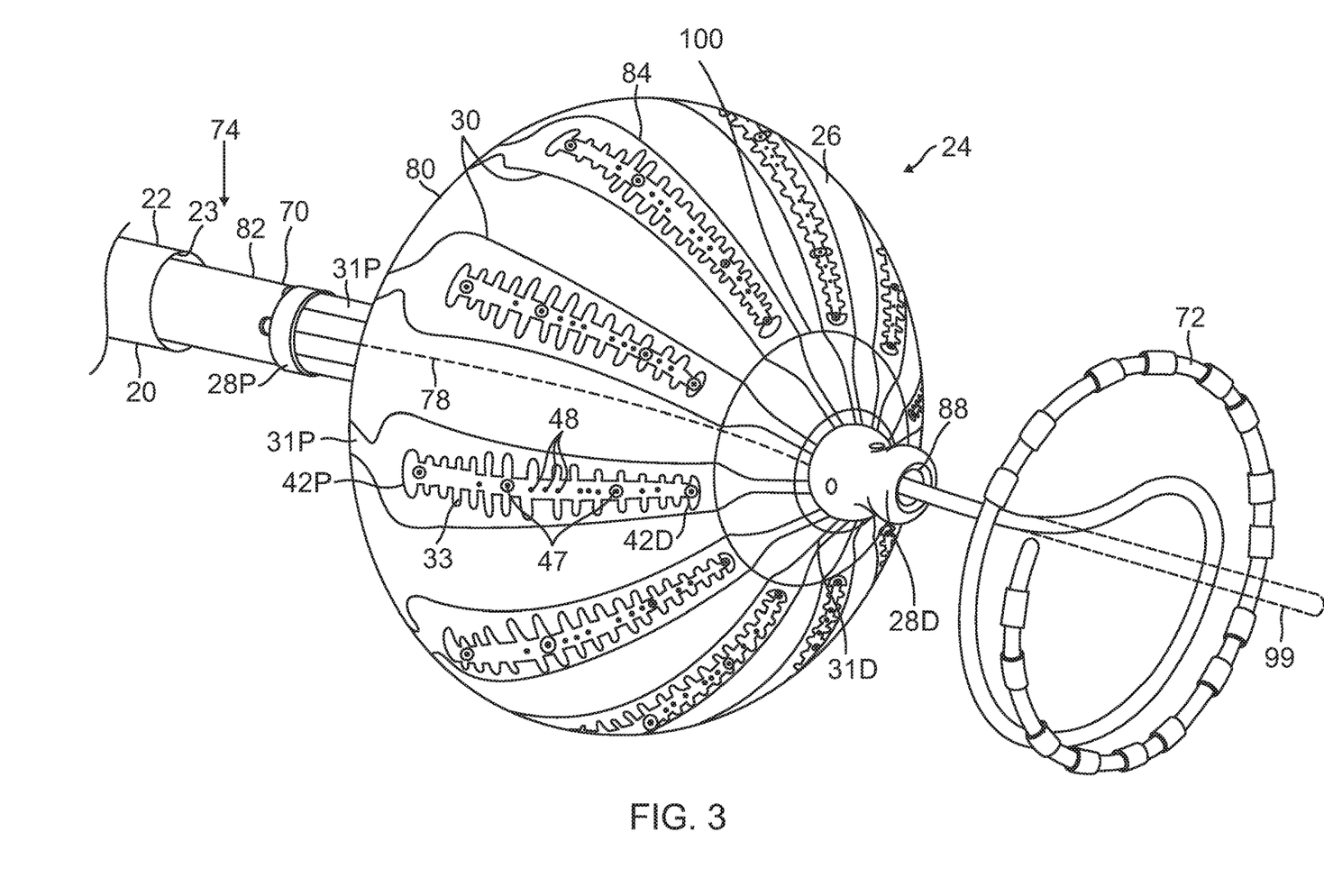
FIG. 3 is a perspective view of a distal end of the catheter of FIG. 2, reflecting the balloon as including a reinforcement component.

FIG. 3 is a schematic perspective view of the diagnostic/therapeutic catheter 24 in an expandable configuration in the form of a balloon in its expanded configuration, according to an embodiment. The diagnostic/therapeutic catheter 24 is supported by a tubular shaft 70 having a proximal shaft portion 82 and a distal shaft end 88. Shaft 70 may include a first shaft portion and a second shaft portion disposed at least partially within the first shaft portion in a telescoping relationship therewith, such that proximal shaft portion 82 is a portion of the first shaft portion and distal shaft end 88 is a distal end of the second shaft. The shaft 70 includes a hollow central tube 74, which permits a catheter to pass therethrough and past the distal shaft end 88. The catheter may be a focal linear catheter or a lasso catheter 72, as illustrated. The lasso catheter 72 may be inserted into the pulmonary vein to position the diagnostic/therapeutic catheter 24 correctly with respect to the ostium prior to ablation of the ostium. The distal lasso portion of the catheter 72 is typically formed of shape-memory retentive material such as nitinol. It is understood that the diagnostic/therapeutic catheter 24 may also be used with a linear or focal catheter 99 (as shown in broken lines in FIG. 3) in the PV or elsewhere in the heart. The focal catheter 99 may include a force sensor at its distal tip. Suitable force sending distal tips are disclosed in U.S. Pat. No. 8,357,152, issued on Jan. 22, 2013 to Govari et al., titled CATHETER WITH PRESSURE SENSING, and in U.S. Patent Application 2011/0130648, to Beeckler et al., filed Nov. 30, 2009, titled CATHETER WITH PRESSURE MEASURING TIP, the entire contents of both of which are incorporated herein by reference. Any catheter used in conjunction with the diagnostic/therapeutic catheter may have features and functions, including, for example, pressure sensing, ablation, diagnostic, e.g., navigation and pacing.

The balloon 80 of the diagnostic/therapeutic catheter 24 has an exterior wall or membrane 26 of a bio-compatible material, for example, formed from a plastic such as polyethylene terephthalate (PET), polyurethane, Pellethane® or PEBAX®. The shaft 70 and the distal shaft end 88 define a longitudinal axis 78 of the balloon 80. The balloon 80 is deployed, in a collapsed configuration, via the lumen 23 of the probe 20, and may be expanded to an expanded configuration after exiting from the distal end 22 by telescoping the first shaft portion relative to the second shaft portion. The membrane 26 of the balloon 80 is formed with irrigation pores or apertures 27 (shown in FIG. 4) through which the fluid (e.g., saline) can exit from the interior of the balloon 80 to outside the balloon for cooling the tissue ablation site at the ostium. While FIG. 2 shows fluid exiting the balloon 80 as jet streams, it is understood that the fluid may exit the balloon with any desired flow rate or pressure, including a rate where the fluid is seeping out of the balloon.

The membrane 26 supports and carries a combined electrode and temperature sensing member which is constructed as a multi-layer flexible circuit electrode assembly 84. The "flex circuit electrode assembly" 84 may have many different geometric configurations. In the illustrated embodiment, the flex circuit electrode assembly 84 has a plurality of radiating substrates or strips 30. The substrates 30 are evenly distributed about membrane 26 of balloon 80. Each substrate has wider proximal portion that gradually tapers to a narrower distal portion.

Each substrate 30 has a proximal tail 31P proximal to the wider proximal portion and a distal tail 31D distal of the narrower distal portion. The proximal tail 31P may be tucked under and fastened to the catheter 24 by a proximal ring 28P mounted on the proximal shaft portion 82 of the shaft 70. The distal tail 31D may be tucked under and fastened to catheter 24 at distal shaft end 88 by distal ring or cap 28D.

Figure 4:
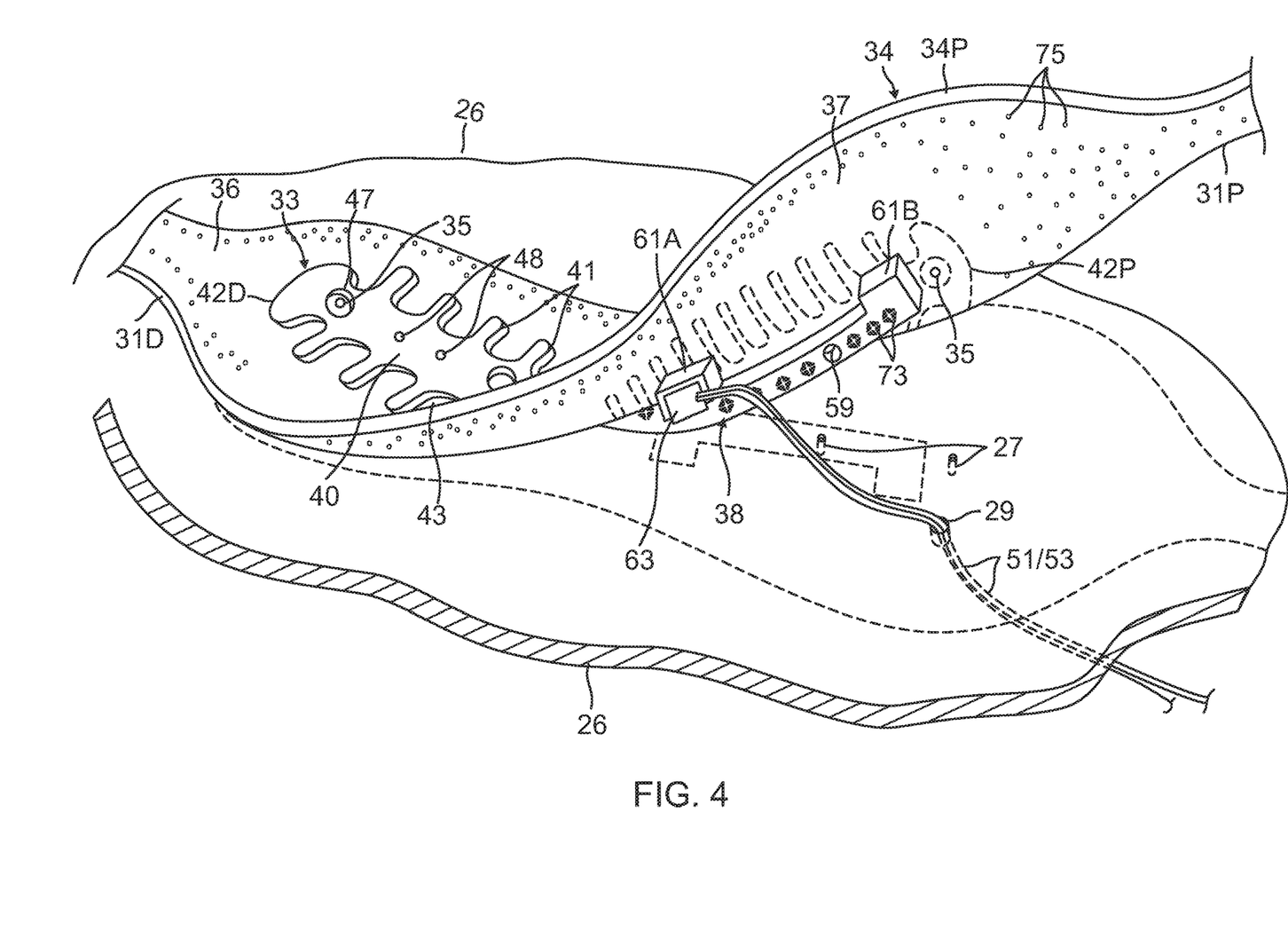
FIG. 4 is a perspective detail view of a flex circuit electrode assembly on the balloon of FIG. 3

For simplicity, the flex circuit electrode assembly 84 is described with respect to one of its substrates 30 as shown in FIG. 4, although it is understood that following description may apply to each substrate of the assembly. The flex circuit electrode assembly 84 includes a flexible and resilient sheet substrate 34, constructed of suitable bio-compatible materials, for example, polyimide. In some embodiments, the sheet substrate 34 has a greater heat resistance (or a higher melting temperature) compared to that of the balloon membrane 26. In some embodiments, the substrate 34 is constructed of a thermoset material having a decomposition temperature that is higher than the melting temperature of the balloon membrane 26 by approximately 100 degrees Celsius or more.

The substrate 34 is formed with one or more irrigation pores or apertures 35 that are in alignment with the irrigation apertures 27 of the balloon member 26 so that fluid passing through the irrigation apertures 27 and 35 can pass to the ablation site on the ostium.

The substrate 34 has a first or outer surface 36 facing away from the balloon membrane 26, and a second or inner surface 37 facing the balloon membrane 26. On its outer surface 36, the substrate 34 supports and carries the contact electrodes 33 adapted for tissue contact with the ostium. On its inner surface 37, the substrate 34 supports and carries a wiring electrode 38. The contact electrode 33 delivers RF energy to the ostium during ablation or is connected to a thermocouple junction for temperature sensing of the ostium. In the illustrated embodiment, the contact electrode 33 has a longitudinally elongated portion 40 and a plurality of thin transversal linear portions or fingers 41 extending generally perpendicularly from each lateral side of the elongated portion 40 between enlarged proximal and distal ends 42P and 42D, generally evenly spaced therebetween. The elongated portion 40 has a greater width and each of the fingers has a generally uniform lesser width. Accordingly, the configuration or trace of the contact electrode 33 may resemble a "fishbone" but it should be noted that the invention is not limited to such configuration. In contrast to an area or "patch" ablation electrode, the fingers 41 of the contact electrode 33 advantageously increase the circumferential or equatorial contact surface of the contact electrode 33 with the ostium while void regions 43 between adjacent fingers 41 advantageously allow the balloon 80 to collapse inwardly or expand radially as needed at locations along its equator. In the illustrated embodiment, the fingers 41 have different lengths, some being longer, others being shorter. For example, the plurality of fingers includes a distal finger, a proximal finger and fingers therebetween, where each of the fingers in between has a shorter adjacent finger. For example, each finger has a length different from its distal or proximal immediately adjacent neighboring finger(s) such that the length of each finger generally follows the tapered configuration of each substrate 30. In the illustrated embodiment, there are 22 fingers extending across (past each lateral side of) the elongated portion 40, with the longest finger being the third finger from the enlarged proximal end 42P. In some embodiments, the contact electrode 33 includes gold with a seed layer between the gold and the membrane 26. The seed layer may include titanium, tungsten, palladium, silver, or combinations thereof.

Formed within the contact electrode 33 are one or more exclusion zones 47, each surrounding an irrigation aperture 35 formed in the substrate 34. The exclusion zones 47 are voids purposefully formed in the contact electrode 33, as explained in detail further below, so as to avoid damage to the contact electrode 33 during construction of the electrode assembly 84 in accommodating the irrigation apertures 35 at their locations and in their function.

Also formed in the contact electrode 33 are one or more conductive blind vias 48 which are conductive or metallic formations that extend through through-holes in the substrate 34 and are configured as electrical conduits connecting the contact electrode 33 on the outer surface 36 and the wiring electrode 38 on the inner surface 37. It is understood that "conductive" is used herein interchangeably with "metallic" in all relevant instances.

In the illustrated embodiment, the contact electrode 33 measures longitudinally between about 0.1 inch and 1.0 inch, and preferably between about 0.5 inch and 0.7 inch, and more preferably about 0.57 inch, and has four exclusion zones 47 and nine blind vias 48.

On the inner surface 37 of the substrate 34, the wiring electrode 38 is generally configured as an elongated body generally similar in shape and size to the elongated portion 40 of the contact electrode 33. The wiring electrode 38 loosely resembles a "spine" and also functions as a spine in terms of providing a predetermined degree of longitudinal rigidity to each substrate 30 of the electrode assembly 84. The wiring electrode 38 is positioned such that each of the blind vias 48 is in conductive contact with both the contact electrode 33 and the wiring electrode 38. In the illustrated embodiment, the two electrodes 33 and 38 are in longitudinal alignment with other, with all nine blind vias 48 in conductive contact with both electrodes 33 and 38. In some embodiments, the wiring electrode 38 has an inner portion of copper and an outer portion of gold.

The wiring electrode 38 is also formed with its exclusion zones 59 around the irrigation apertures 35 in the substrate 34. The wiring electrode 38 is further formed with solder pad portions 61, at least one active 61A, and there may be one or more inactive solder pad portions 61B. The solder pad portions 61A and 61B are extensions from a lateral side of the elongated body of the wiring electrode 38. In the illustrated embodiment, an active solder pad portion 61A is formed at about a mid-location along the elongated body, and a respective inactive solder pad portion 61B is provided at each of the enlarged distal end 42D and the enlarged proximal end 42P.

Attached, e.g., by a solder weld 63, to the active solder pad portion 61A are the wire pair, e.g., a constantan wire 51 and a copper wire 53. The copper wire 53 provides a lead wire to the wiring electrode 33, and the copper wire 53 and the constantan wire 51 provide a thermocouple whose junction is at solder weld 63. The wire pair 51/53 are passed through a through-hole 29 formed in the membrane 26. It is understood that, in other embodiments in the absence of the through-hole 29, the wire pair 51/53 may run between the membrane 26 and the substrate 34 and further proximally between the membrane 26 and the proximal tail 31P until the wire pair 51/53 enters the tubular shaft 70 via another through-hole (not shown) formed in the tubular shaft sidewall closer to the proximal ring 28P.

The flex circuit electrode assembly 84, including the substrates 30 and the tails 31P and 31D, is affixed to the balloon membrane 26 such that the outer surface 36 of the substrate 34 is exposed and the inner surface 37 of the substrate 34 is affixed to the balloon membrane 26, with the wiring electrode 38 and wire pair 51/53 sandwiched between the substrate 34 and the balloon membrane 26. The irrigation apertures 35 in the substrate 34 are aligned with the irrigation apertures 27 in the balloon membrane 26. The exclusion zones 59 in the wiring electrode 38 and the exclusion zones 47 in the contact electrode 33 are concentrically aligned with each other, as well as with the irrigation apertures 27 and 35 in balloon 26 and substrate 34, respectively.

Further details on constructing a diagnostic/therapeutic catheter in accordance with the foregoing disclosure may be found in U.S. patent application Ser. No. 15/360,966, published as U.S. Patent Application Publication No. 2017/0312022, which is incorporated by reference herein in its entirety.

REINFORCEMENT

Through ongoing research and product development efforts concerning the subject matter described above, Applicant has determined that balloon 80 must be able to withstand multiple cycles of being deployed from lumen 23 of probe 20 in the collapsed configuration, expanded to the expanded configuration, returned to the collapsed configuration and withdrawn into lumen 23 of probe 20. The number of cycles may be from about five to about twenty. That is, the connection between substrate 30 and membrane 26 of balloon 80 and overall integrity of the assembled balloon must withstand at least five to twenty fatigue cycles and any additional frictional stresses experienced during five to twenty deployments from and five to twenty withdrawals into lumen 23. Applicant believes that there is a very small likelihood of potential delamination of proximal tails 31P and distal tails 31D from membrane 26, which could arise from repeated fatiguing and has implemented a solution that would prevent, or at least significantly further lower the likelihood of, any such delamination. Applicant further determined that any such solution would need to accommodate for various design constraints, such as: 1) minimizing concomitant safety concerns caused by any solution; 2) minimizing any increase to diameter of the portions of balloon 80 upon which distal tails 31D and proximal tails 31P are adhered such that balloon 80 in the collapsed configuration may be readily deployed from and withdrawn into lumen 23 with little or no increase in friction therebetween (or especially, in the extreme, avoiding a need to increase the diameter of lumen 23); 3) minimizing any increase to the stiffness of balloon 80, which could interfere with establishing contact between electrode 30 and tissue during a procedure; 4) not impeding electrical contact between electrodes 33 and tissue during a procedure; and 5) minimizing an increase to the number of assembly steps.

Figure 6:
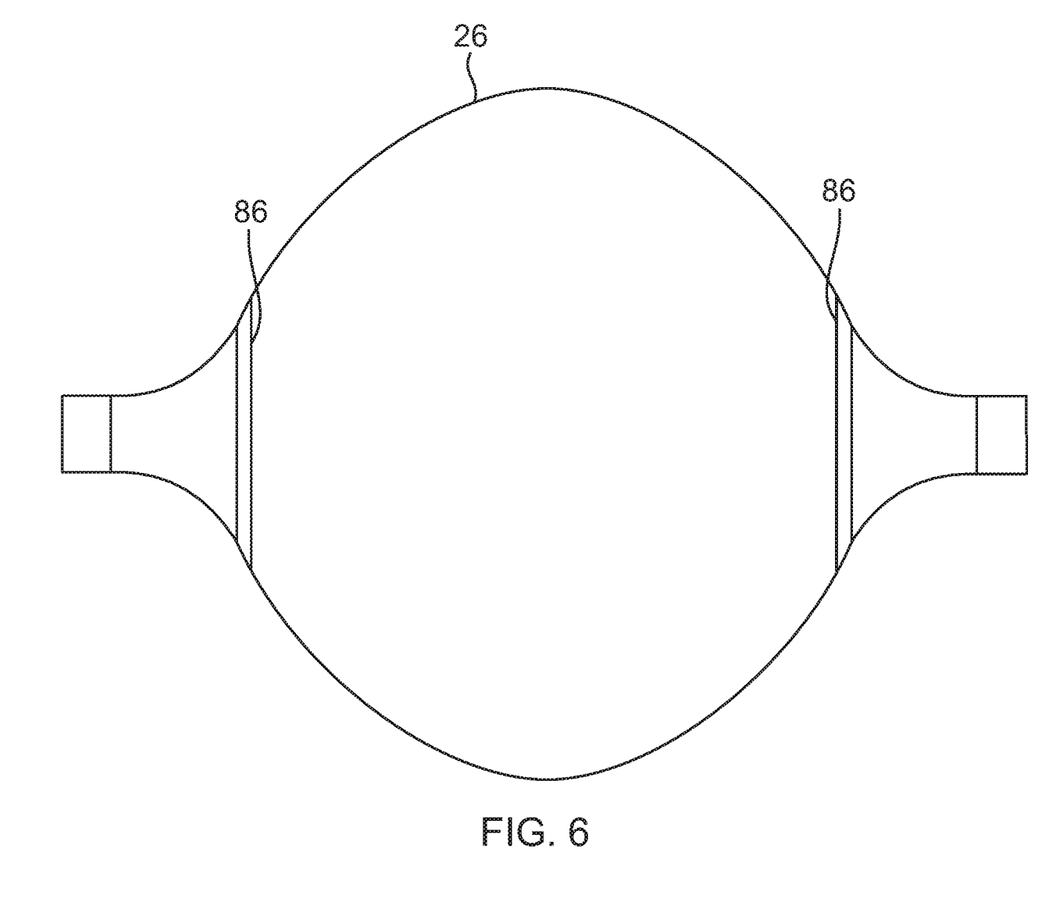
FIG. 6 is a side view of an unassembled balloon component.
Figure 7:
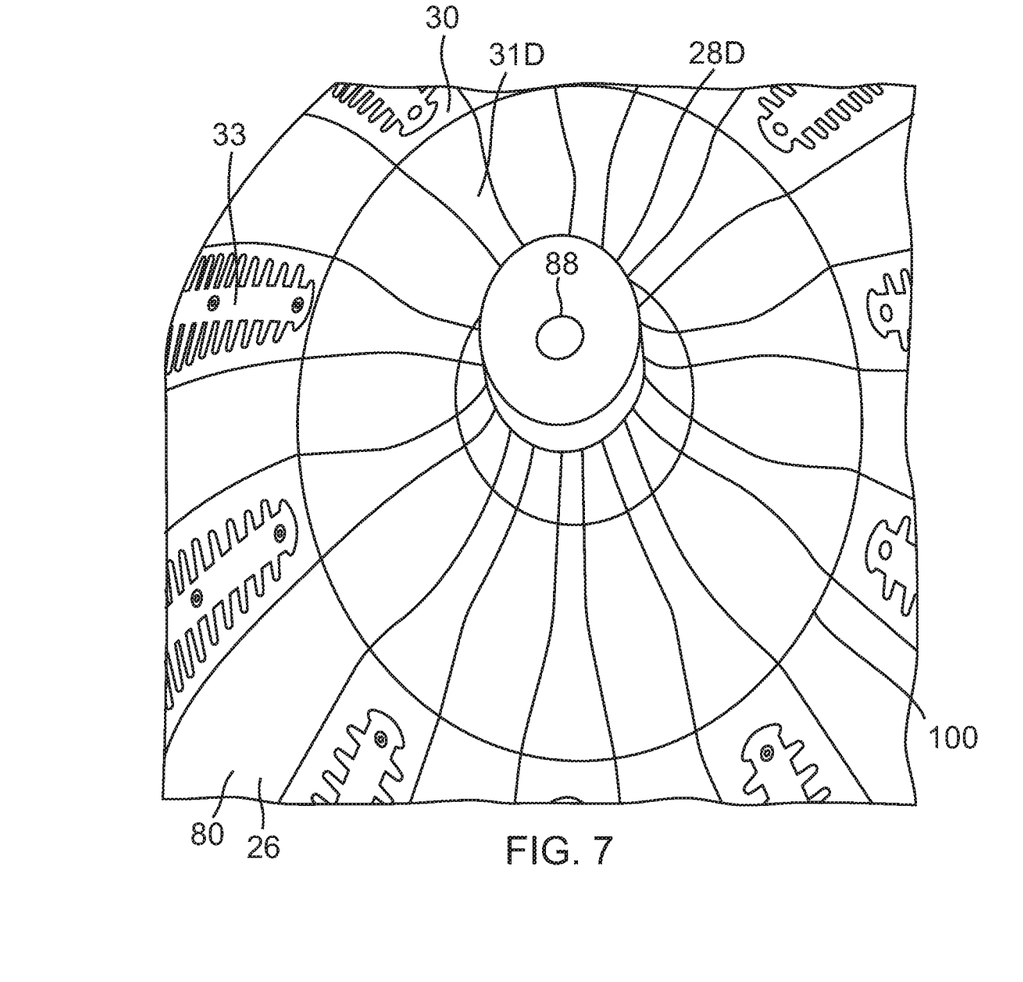
FIG. 7 is a detail view of the distal end of the catheter of FIG. 3.

Disclosed herein is a reinforcement or reinforcement component 100 that assists in preventing the delamination problem without violating the design constraints. Reinforcement component 100 may have a shape like and thus conform to a proximal or distal portion of membrane 26. For example, reinforcement component 100 may include a portion of an unassembled catheter balloon 80, i.e., a balloon 80 that has not been assembled to any other components of catheter 24, such as substrates 30. That is, a balloon 80 may have a portion separated therefrom by cutting membrane 26 along one of the lines 86 as seen in FIG. 6. In embodiments where balloon 80 is symmetric about a center line, two portions of balloon 80 may be removed to create two reinforcement components 100. In embodiments where membrane 26 is asymmetric about a center line, the distal portion thereof may be used as reinforcement component 100 for distal tails 31D and the proximal portion thereof may be used as reinforcement component 100 for proximal tails 31P.

Figure 5:
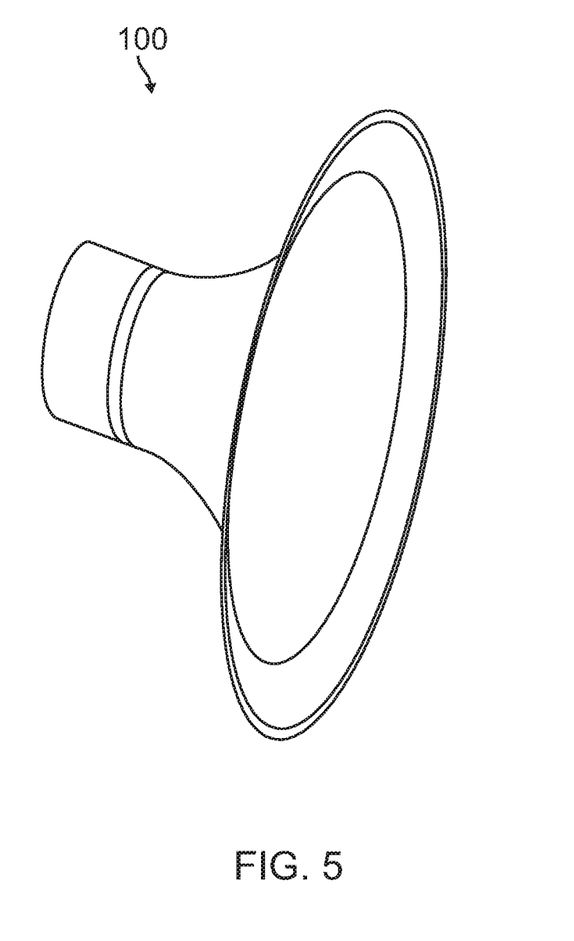
FIG. 5 is a perspective view of the reinforcement component of FIG. 3.

Thus, reinforcement component 100 may be provided as having a horn-like (e.g., bell-mouth) shape as seen in FIG. 5. Membrane 26, with flexible circuit assembly 84 adhered thereto, may have its proximal portion disposed within reinforcement component 100 such that reinforcement component 100 covers proximal tails 31P or a portion thereof. Alternatively, or additionally, membrane 26, with flexible circuit assembly 84 adhered thereto, may have its distal portion disposed within reinforcement component 100 such that reinforcement component 100 covers distal tails 31D or a portion thereof. Reinforcement component(s) 100 may then be adhered to membrane 26 via e.g., epoxy, or mechanical or thermal fusion. Accordingly, the tails are sandwiched between balloon 80 and reinforcement component 100. In this configuration reinforcement component 100 may absorb stresses caused by expanding and collapsing balloon 80, thereby reducing fatigue to the tails. Further, the tails are shielded from friction between reinforcement component 100 and walls of lumen 23, that would otherwise exist between the tails and the walls of lumen 23 during deployment and withdrawal, thereby further reducing stresses upon the tails.

In further embodiments, the likelihood of delamination may be further reduced by supporting one or more of the tails (e.g., all of the tails) with a length of filament between membrane 26 and a respective tail 31P or 31D. Ideally the filament material is one that bonds readily to both the substrate material and the membrane material, such that the filament may increase the robustness of the connection between the tails and the membrane. Suitable materials include liquid crystal polymers, such as VECTRAN™ or preferably Ultra-High Molecular Weight Polymer such as Honeywell SPECTRA™.

By virtue of the embodiments illustrated and described herein, applicant has devised a method of using a diagnostic/therapeutic catheter having a balloon upon which is disposed various components suitable for ablating tissues, the method including repeated steps that may stress connections between the balloon and the catheter. Specifically, a catheter, such as the one heretofore described (e.g., catheter 24) may be received by a user. The user may deploy the balloon from the catheter, expand the balloon, collapse the balloon, and withdraw the balloon into the catheter. These steps may be repeated between five to fifteen, e.g., ten times. Moreover, the user may use electrodes disposed on the balloon to ablate tissue, typically between the steps of expanding and collapsing the balloon.

Any of the examples or embodiments described herein may include various other features in addition to or in lieu of those described above. The teachings, expressions, embodiments, examples, etc. described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but, in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A catheter balloon, comprising:
   a membrane including a proximal end and a distal end;
   a plurality of substrates disposed about the membrane, each of the plurality of substrates including a respective proximal tail disposed over and in contact with the proximal end of the membrane, and a respective distal tail disposed over and in contact with the distal end of the membrane;
   a first reinforcement comprising a first portion of an unassembled catheter balloon disposed over and in contact with each of the respective proximal tails of each of the plurality of substrates and attached to the proximal end of the membrane; and
   a second reinforcement comprising a second portion of the unassembled catheter balloon disposed over and in contact with each of the respective distal tails of each of the plurality of substrates and attached to the distal end of the membrane.

2. The catheter balloon of claim 1, in which the first reinforcement has a horn-like shape.

3. The catheter balloon of claim 2, in which the membrane comprises polyethylene terephthalate or polyurethane.

4. The catheter balloon of claim 2, in which the first reinforcement is symmetric with the second reinforcement.

5. The catheter balloon of claim 4, in which the membrane further includes irrigation apertures disposed therethrough.

6. The catheter balloon of claim 4, further comprising a plurality of ablation electrodes.

7. The catheter of claim 6, in which at least one of the plurality of ablation electrodes is disposed on each of the plurality of substrates.

8. The catheter balloon of claim 4, further comprising a filament disposed between the membrane and at least one of the respective distal tails.

9. The catheter balloon of claim 8, in which the filament comprises a liquid-crystal polymer.

10. A catheter, comprising:
    a shaft having a first shaft portion and a second shaft portion at least partially disposed within the first shaft portion;
    a catheter balloon having a membrane including a proximal end and a distal end, the proximal end disposed over and connected to the first shaft portion and the distal end disposed over and connected to the second shaft portion;
    a plurality of substrates disposed about the membrane, each of the plurality of substrates including a respective proximal tail disposed over and attached to the first shaft portion, and a respective distal tail disposed over and attached to the second shaft portion;
    a first reinforcement comprising a first portion of an unassembled catheter balloon disposed over and in contact with each of the respective proximal tails of each of the plurality of substrates and attached to the proximal end of the membrane; and
    a second reinforcement comprising a second portion of the unassembled catheter balloon disposed over and in contact with each of the respective distal tails of each of the plurality of substrates and attached to the distal end of the membrane.

11. The catheter of claim 10, further comprising a first ring attaching the first reinforcement to the first shaft portion and a second ring attaching the second reinforcement to the second shaft portion.

12. The catheter of claim 11, in which the first reinforcement has a horn-like shape.

13. The catheter of claim 12, in which the second shaft portion is disposed within the first shaft portion in a telescoping relationship.

14. The catheter of claim 12, further comprising a plurality of ablation electrodes.

15. The catheter of claim 14, in which at least one of the plurality of ablation electrodes is disposed on each of the plurality of substrates.

16. The catheter of claim 14, further comprising a lead wire at least partially disposed in the shaft and in the catheter balloon, and connected to at least one of the plurality of ablation electrodes.

17. The catheter of claim 12, further comprising a filament disposed between the membrane and at least one of the respective distal tails.

18. The catheter of claim 17, in which the filament comprises one of an ultra-high molecular weight polymer or a liquid-crystal polymer.

19. The catheter of claim 12, in which the membrane comprises polyethylene terephthalate or polyurethane.

* * * * *